United States Patent [19]

McCall

[11] 4,167,567
[45] Sep. 11, 1979

[54] ANTIHYPERTENSIVE 4-AMINOQUINOLINES

[75] Inventor: John M. McCall, Kalamazoo, Mich.

[73] Assignee: The Upjohn Company, Kalamazoo, Mich.

[21] Appl. No.: 903,082

[22] Filed: May 5, 1978

[51] Int. Cl.$^2$ ............... A61K 31/495; C07D 401/12; C07D 401/14

[52] U.S. Cl. ................... 424/250; 424/249; 424/251; 544/212; 544/295; 544/357; 544/363

[58] Field of Search ............ 544/363, 212, 295; 424/250

[56] References Cited

U.S. PATENT DOCUMENTS

| | | | |
|---|---|---|---|
| 3,362,956 | 1/1968 | Archer | 544/363 |
| 3,632,761 | 1/1972 | Graham | 544/363 |
| 4,025,629 | 5/1977 | Coverdale | 424/250 |

Primary Examiner—Paul M. Coughlan, Jr.
Attorney, Agent, or Firm—Robert A. Armitage; Hans L. Berneis

[57] ABSTRACT

Antihypertensive compounds of the formula ll

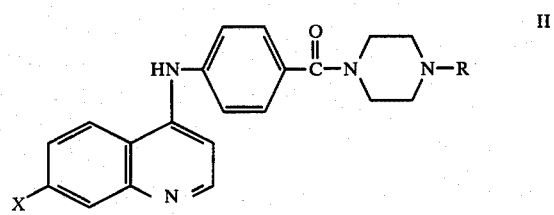

wherein X is chloro or trifluoromethyl; wherein R is an aromatic heterocyclic radical selected from the group consisting of triazinyl, pyrazinyl, pyridinyl, pyrimidinyl or the above radicals substituted by one or two trifluoromethyl, alkyl, alkoxy, dialkylamino, alkylthio, or halo, or 1 to 4 halo atoms for pyridine, or combinations of substituents, in which alkyl and alkoxy are each of 1 to 3 carbon atoms, inclusive, and halo is fluoro, bromo or chloro, or R is the group

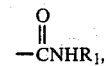

in which $R_1$ is phenyl, phenyl-substituted with one or two halogens, trifluoromethylphenyl, phenyl-substituted with one or two alkoxy or alkyl groups, or alkylphenylsulfonyl, in which alkyl, alkoxy, and halo are defined as above; or R is the group $SO_2R_2$, in which $R_1$ is dialkylamino, phenyl, phenyl-substituted with one or two halogens, alkyl, trifluoromethyl or alkoxy groups, in which alkyl, alkoxy and halo are defined as hereinabove, are prepared from compounds of the formula

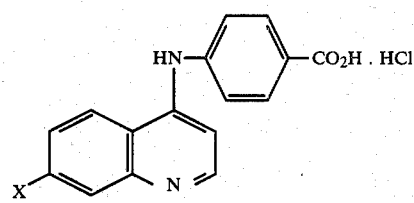

wherein X has the significance as above, by reaction with the selected cyclic amine or by reaction of

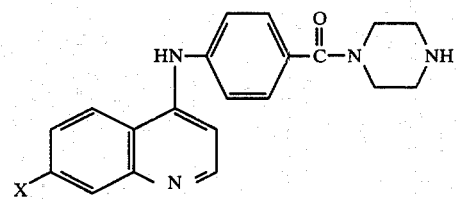

wherein X is defined as above and a selected $R_2$-sulfonyl chloride or $R_1$-isocyanate.

The compounds of formula ll and their pharmacologically acceptable acid addition salts are hypotensive agents which are useful for the treatment of hypertension in mammals, including man.

39 Claims, No Drawings

ANTIHYPERTENSIVE 4-AMINOQUINOLINES

BRIEF SUMMARY OF THE INVENTION

Field of the Invention

This invention concerns new organic compounds, in particular, 1-substituted-4-(quinolinylaminobenzoyl)-piperazines II, their use as antihypertensives, and their formulations.

The new compounds and the process of this invention can be illustratively represented by the following schemes:

Scheme A

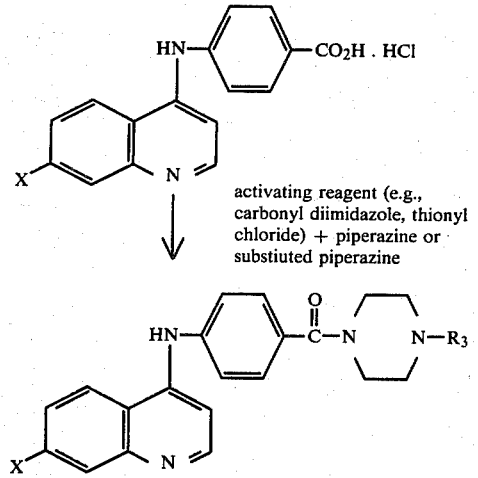

Scheme B

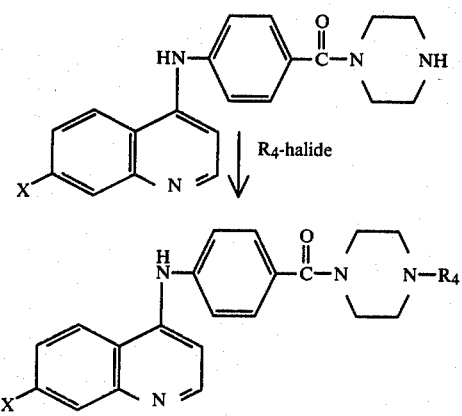

Scheme C

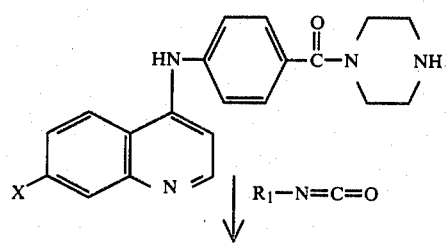

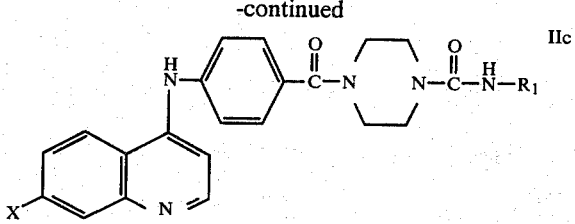

wherein X is chloro or trifluoromethyl; wherein $R_3$ is pyridinyl or pyridinyl-substituted by one or two alkyl, alkoxy, trifluoromethyl, in which alkoxy and alkyl are of 1 to 3 carbon atoms, inclusive; wherein $R_4$ is pyrazinyl, pyridinyl, pyrimidinyl, triazinyl, per se, or substituted by one or two alkyl, alkoxy, dialkylamino, trifluoromethyl, alkylthio radicals, or 1 or 2 halo groups with the proviso that pyridinyl may have from 1 to 4 halo atoms, inclusive, or combinations of these substituents, in which alkyl and alkoxy are each of 1 to 3 carbon atoms, inclusive, and halo is bromo, chloro or fluoro; $R_4$ is $SO_2R_2$ in which $R_2$ is dialkylamino, phenyl-substituted with one or two halogens, alkylphenyl, phenyl, trifluoromethylphenyl, and phenyl-substituted with one or two alkoxy groups in which alkyl, alkoxy and halo are defined as above; and $R_1$ is phenyl, trifluoromethylphenyl, alkylphenyl, alkylphenylsulfonyl, phenyl-substituted with one or two halo groups, or phenyl-substituted with one or two alkoxy groups.

The new compounds, therefore, embraced by this invention are selected from the group of compounds of generic structure

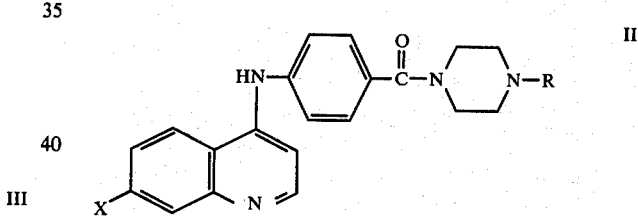

wherein X is chloro or trifluoromethyl; wherein R is an aromatic heterocyclic radical selected from the group consisting of triazinyl, pyrazinyl, pyridinyl, pyrimidinyl or the above radicals substituted by one or two trifluoromethyl, alkyl, alkoxy, dialkylamino, alkylthio, one or two halo atoms with the proviso that pyridinyl may have 1 to 4 atoms, or cimbintions of substituents, in which alkyl and alkoxy are each of 1 to 3 carbon atoms, inclusive, and halo is fluoro, bromo, or chloro; or R is the group

in which $R_1$ is phenyl, phenyl substituted with one or two halogens, trifluoromethyl, alkyl, alkoxy groups or alkylphenylsulfonyl, in which alkyl, alkoxy, and halo are defined as above; or R is the group $SO_2R_2$, in which $R_2$ is dialkylamino, phenyl, phenyl-substituted with one or two halogens, alkyl, trifluoromethyl or alkoxy groups, in which alkyl, alkoxy and halo are defined as hereinabove, or the pharmacologically acceptable acid addition salts of compound II.

The more preferred compounds of this invention are selected from the group consisting of the compounds of the formula IIA

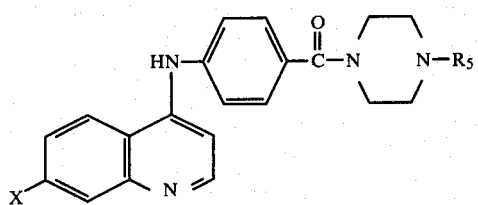

wherein X is chloro or trifluoromethyl; $R_5$ is pyridinyl, pyrimidinyl, and pyrazinyl or the alkylthio-, alkyl-, halo- or alkoxy-substituted derivatives thereof, in which halo is chloro or fluoro and alkyl and alkoxy are of one to three carbon atoms, inclusive; or $R^5$ is —$SO_2R_6$, in which $R_6$ is phenyl, alkylphenyl, halophenyl, alkoxyphenyl, alkyl, alkoxy and halo being defined as above; or $R_5$ is

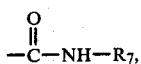

in which $R_7$ is phenyl, alkylphenyl, halophenyl, trifluoromethylphenyl, or alkylphenylsulfonyl, in which halo and alkyl are defined as above, or the pharmacologically acceptable acid addition salts thereof.

The most preferred compounds of this invention are selected from the group consisting of compounds of the formula IIB

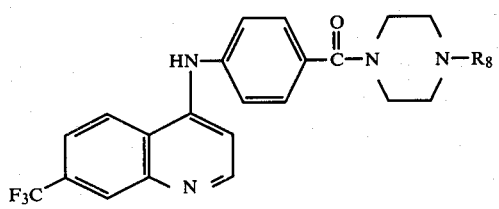

wherein $R_8$ is pyrimidinyl, pyridinyl, and pyrazinyl or these groups substituted with methyl, methylthio, methoxy or chloro; or $R_8$ is —$SO_2R_9$, in which $R_9$ is

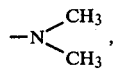

p-tolyl, p-chlorophenyl or p-fluorophenyl; or $R_8$ is

in which $R_{10}$ is halophenyl, phenyl or trifluoromethylphenyl, in which halo is chloro or fluoro, and the pharmacologically acceptable acid addition salts thereof.

The following patents are considered related to the present invention: U.S. Pat. Nos. 3,632,761; 3,992,382; 4,025,629; and British Patent specification No. 1,435,863.

However, the compounds of the present invention have structural differences since they have different substituents on the piperazine unit. Though all patents cited above show the piperazine moiety, the substituents in the 1-position of the piperazine ring in this invention are distinct from those in the cited patents above.

It has now been found that the piperazine group, although very favorable to the reduction of blood pressure, can cause, if unsubstituted, cataracts in rats. Compounds of formula II produce the desirable reduction of blood pressure in hypertensive patients without the danger of cateracts.

The reactions to produce these compounds are according to:

Scheme A: A single step reaction of 4-[7-chloro(or trifluoromethyl)-4-quinolinyl]aminobenzoic acid hydrochloride I with thionyl chloride which produces the acid chloride, or with carbonyl diimidazole, which produces an imidazolide; this is then condensed with a cyclic amine

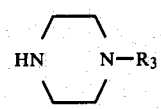

wherein $R_3$ is a pyridinyl moiety, which may be substituted by trifluoromethyl or alkyl or alkoxy, of 1 to 3 atoms, inclusive.

A more widely utilized process is the process:

Scheme B: 1-[p-[[(7-chloro (or trifluoromethyl)-4-quinolyl]amino]benzoyl]piperazine III is reacted with a chloro or bromoheterocyclic aromatic compound or a sulfonyl chloride in the presence of a base to give the compound IIb series.

Scheme C: In this Scheme, compounds of the formula IIc are produced by reacting compounds of the formula II with an isocyanate.

Isolation and purification of the compounds of this invention are carried out by conventional means using chromatography (when necessary), recrystallization, etc.

On occasion, the compounds or their acid addition salts in their crystalline state are isolated as solvates, i.e., they have discrete quantity of solvent, e.g., water, ethanol and the like, associated physically, and thus removable without effective alteration of the chemical entity per se. The invention is meant to encompass all such forms of the compounds.

PREFERRED EMBODIMENT OF THE INVENTION

The alkyl groups in this invention, having 1 to 3 carbon atoms, inclusive, comprise methyl, ethyl, propyl, isopropyl, with methyl preferred.

The preferred halogens are chloro and fluoro.

The pharmacologically acceptable acid salts of compound of the formula II comprise the hydrochlorides, hydrobromides, hydriodides, sulfates, phosphates, cyclohexanesulfamates, pamoates, methanesulfonates and the like, prepared by contacting a compound of formula II with the stoichiometrically calculated amount of the selected pharmacologically acceptable acid.

The compounds were tested for hypotensive activity and for cataractogenic activity.

The hypotensive activity of the new compounds was determined by measuring the mean arterial blood pressure at different dosage levels in the rat and determining from it the mean blood pressure reduction after 4 and 24 hours.

The mean arterial blood pressure is defined in the art as:

$$\frac{\text{systolic pressure} - \text{diastolic pressure}}{3} + \text{diastolic pressure}$$

Also, decrease of the heart rate at 4 and 24 hours after drug administration was determined.

The following is a brief description of the procedures and the basis of reporting compounds as active or inactive hypotensive agents in the assay.

Methods: Chronic abdominal aortic indwelling cannula are exteriorized t the nape of the neck of Upjohn Sprague Dawley specific pathogen free female rats. Aortic blood pressure is monitored with a transducer-polygraph system. Mean arterial blood pressure is obtained by electrical integration of phasic pressure. Heart rate is obtained by electronically counting arterial pulses. Two unanesthetized rats are each treated orally with single 50 mg/kg doses of the test compound. Test agents are suspended in Upjohn Vehicle 98 [each ml of water contains carboxymethylcellulose (10 mg), polysorbate 80 (4 mg) and polyparaben (0.42 mg)] or an appropriate carrier. Injection volume is 10 cc/kg. Mean arterial blood pressure and heart rate are observed before, and 4 and 24 hours after drug administration. Results: Blood pressures of 2 rats are averaged before, and 4 and 24 hours after oral treatment with the test compound. If the change, initial vs 4 and/or 24 hours, is <5 mm Hg the compound is considered inactive. Average change is then calculated for 2 rats. If the decrease is ≧5 mm Hg, the compound is considered to be an active hypotensive agent.

Heart rates are also obtained before, and 4 and 24 hours after drug administration. If the average change, initial vs 4 and/or 24 hours, is <65 beats per minute the compound is not considered to have altered the heart rate. If the average change is ≧65 beats per minute, the compound is considered to have altered heart rate.

By far the majority of the compounds of this invention show blood pressure reductions of greater than 10 mm Hg at 4 or 24 hours.

It has been found that two compounds (of formula IV, below) containing the quinolinyl function, while reducing the blood pressure, at the same time caused the development of cataracts in rats.

An in vitro test was found to test for this undesirable cataractogenic activity of compounds. A description of this method can be found in Edwards et al., Experimental Eye Research, 10, 228 (1970).

MATERIALS AND METHODS

Under sterile conditions, the commercial Grand Island Biologicals Co. Medium #199 containing phenol red at a concentration of 0.002% was diluted 1:10 with sterile distilled water. The diluted Medium #199 was then supplemented with foetal calf serum (10%, v/v), 100 units/ml of penicillin, and 100 mg/ml of streptomycin. The final pH of this growth medium was adjusted with sterile 0.5 N sodium hydroxide.

Compounds to be tested were dissolved or suspended at a concentration of 15 mM in Vehicle 124 (0.25% methylcellulose in isotonic saline) containing 10% diluted Medium #199. When necessary, pH adjustments were made to maintain the pH at 7.2.

Eyes were removed from 11-13 day chick embryos in a sterile surface hood. All subsequent steps employed sterile techniques. Lenses were removed and greed of adhering humor. Each lens was then placed into a sterile 12×75 mm test tube containing the incubation medium described above. After all lenses were removed, an aliquot (10-100 μl) of Vehicle 124 containing Medium #199 with or without test compound was added to a final volume of 300 μl. Paired lenses were incubated with different drugs. Each tube was stoppered with gaze-wrapped paper plugs and incubated at 36° C. Lenses were incubated for four hours after which the incubation medium containing the drug was removed by aspiration. Lenses were rinsed once with growth medium and that medium removed; 300 μl of fresh growth medium free of drug was added to the lens and the incubation was continued at 36° C. The pH changes in the growth media were determined semi-quantitatively by color comparison of the tube with a set of standard solutions prepared over the range of 4 to 8 and containing the same concentration of phenol red as in the growth medium.

| Color | Purple | Pink | Slightly Pink | Slightly Orange | Orange | Gold | Light Gold | Yellow |
|-------|--------|------|---------------|-----------------|--------|------|------------|--------|
| pH | 8 | 7.2–7.4 | 5.5 | 5 | 6 | | 5 | 4.5 | 4 |

Color comparisons were made after 17-19 hours, 24 hours and 48 hours. In some experiments comparisons were also made at longer intervals.

As a result of the metabolism by the lenses during incubation, principally due to lactic acid formation, a decrease of the pH and change of color of the indicator from pink to yellow is observed. A compound such as:

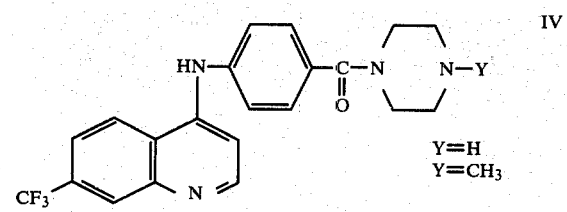

IV

Y=H
Y=CH₃

(Y=H) completely blocks the metabolism which causes the pink coloration to remain. The same compound wherein, however, Y is methyl, also produces cataracts in rats. Thus, by colorometric comparison between pH 4 to 8 of prepared standard solutions any degree of cataractogenic activity is discovered. The compounds of this invention did not inhibit respiration.

This invention relates also to pharmaceutical dosage unit forms for systemic administration of compounds of formula II (oral and parenteral administration) in obtaining unexpectedly advantageous beneficial results in hypertensive conditions in mammals (including humans) and valuable warm-blooded animals such as dogs, cats, and other domestic animals. The term "dosage unit form" as used in this specification and in the claims refers to physically discrete units suitable as unitary dosages for mammalian subjects, each unit containing a predetermined quantity of the essential active ingredient calculated to produce the desired effect in combination with the required pharmaceutical means which adapt the said ingredient for systemic administration. The specification for the novel dosage unit forms of this invention are dictated by and directly dependent on the unique characteristics of the essential active ingredient and the particular effect to be achieved in view of the limitations inherent in the art of compounding such as essential active material for beneficial effects in humans and animals as disclosed in detail in this specification under preferred embodiments, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn starch, talc and the like. Capsules both hard and soft are formulated with suitable diluents and excipients, for example, edible oils, talc, calcium carbonate and the like, and also calcium stearate. Liquid preparations for oral administration are prepared in water or aqueous solutions which advantageously contain suspending agents, for example, sodium carboxymethylcellulose, methylcellulose, acacia, polyvinyl pyrrolidone, polyvinyl alcohol and the like. In the case of injectable forms, they must be sterile and must be fluid to the extent that easy syringeability exists. Such preparations must be stable under the conditions of manufacture and storage, and ordinarily contain, in addition to the basic solvent or suspending liquid, preservatives in the nature of bactericidal and fungicidal agents, for example, parabens, chlorobutanol, benzyl alcohol, phenol, and the like. In many cases it is preferable to include isotonic agents, for example, sugars or sodium chloride. Carriers and vehicles include vegetable oils, ethanol, polyols, for example, glycerol, propylene glycol, liquid polyethylene glycol and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 5 to about 100 mg of the essential active ingredient per dosage unit form, which, as aforesaid, may be in the form of a solid oral preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain antihypertensive effects within the effective nontoxic range. Expressed otherwise, an amount of the essential active ingredient is provided to a recipient within a range from about 0.05 mg per kg to about 20 mg per kg of body weight of the recipient, preferably 0.1 to 10 mg per kg; the most preferred dose range is 0.2 to 5 mg per kg.

The amount administered depends on the age, weight, and condition of the patient as determined by the physician.

The starting compound of this invention 4-[[7-(trifluoromethyl)-4-quinolinyl]amino]benzoic acid is commercially available. The acid chloride thereof is prepared by the conventional method of treating at reflux the acid with sulfonyl chloride (4½ hours of reflux). The compound 4-[4-[[7-(trifluoromethyl)-4-quinolinyl]amino]benzoyl]piperazine can be prepared by reacting piperazine with the chloride or by the method of U.S. Pat. No. 4,025,629 (Example 8).

The final desired products are prepared as shown by Schemes A, B, and C discussed in previous pages, or as particularly disclosed in the subsequent examples.

The syntheses of other starting materials are described in the preparations.

Preparation 1:
4-[4-[[7-chloro-4-quinolinyl]amino]benzoyl]piperazine (a) p-Nitrobenzoylpiperazine [Method of: Austral. J. Chem. I, 397 (1956)].

A solution of 39.0 g (0.2 mole) of piperazine hexahydrate in 800 ml of water is treated with 60 drops of bromocresol green indicator and then to it is added 41 ml of 10 N hydrochloric acid which makes the reaction solution a bluish-green. One liter of acetone is added followed by 74.0 g (0.4 mole) of p-nitrobenzoyl chloride, and a solution of 45.0 g (0.8 mol) of potassium hydroxide in 200 ml of water. The addition is dropwise with rapid stirring over a 10-minute period keeping the color of the solution green. After the addition is complete, the acetone is distilled off (760 mm) and the residual solution acidified to pH 1.5 with 10 N hydrochloric acid and cooled to 0° C. A precipitate forms which is collected and dried to give 43.7 g of a compound of m.p. 229°–236.5° C.

The filtrate is basified with solid potassium carbonate and extracted with 10×250 ml of chloroform and the chloroform dried over anhydrous sodium sulfate. Filtration and concentration in vacuo give 33.04 g of yellow granular crystals of p-nitrobenzoylpiperazine, m.p., 158.5°–160° C. (70% yield).

Calcd. for $C_{11}H_{13}N_3O_3$: Calcd.: C, 56.16; H, 5.57; N, 17.86. Found: C, 65.20; H, 5.61; N, 18.01.

(b) p-Aminobenzoylpiperazine

A mixture of 11.75 g (0.05 mole) of p-nitrobenzoylpiperazine in 150 ml of absolute methanol and 0.2 g of 10% palladium on carbon is hydrogenated on a Parr apparatus during which the calculated amount of hydrogen is taken up over a 1.5 hour period. The reaction is left to stand overnight at room temperature. The reaction mixture is filtered from the catalyst and the filtrate concentrated in vacuo giving a near white crystalline residue. This residue is re-crystallized from 1-propanol at the boiling point giving 9.51 g of near-white crystals of melting point 194.5°–195.5° C.

Calcd. for $C_{11}H_{15}N_3O_3$: Calcd.: C, 64.36; H, 7.37; N, 20.47. Found: C, 64.26; H, 7.50; N, 20.26.

(c) 4-[4-[[7-chloro-4-quinolinyl]amino]benzoyl]piperazine

A mixture of 9.9 g of 4,7-dichloroquinoline, 10.25 g (0.05 mole) of p-aminobenzoylpiperazine, 50 ml of ethanol and 4.25 ml of 12 M hydrochloric acid is warmed to reflux with magnetic stirring and after reaching reflux temperature the reaction mixture goes into solution. The solution is refluxed overnight (17.0 hours); the reaction mixture is still a solution but upon slight cooling, solid forms. The reaction mixture is refluxing for a total time of 24.0 hours and then left to stand for two days at room temperature. The reaction mixture is concentrated in vacuo, slurried with 150 ml of water, and reconcentrated. The residue is slurried with 150 ml of water and filtered from a trace of insoluble solid. The filtrate is treated with 65 ml of 2 N sodium hydroxide. A large amount of solid forms. This alkaline solution is well-extracted with CHCl₃ and the CHCl₃ phase dried over anhydrous Na₂SO₄. The inorganic layer is then filtered from a tan solid which is insoluble in chloroform. This is dried at 40° C. in a vacuum oven to give 10.06 g of compound with melting point 246.5°–249° C. Filtration and concentration in vacuo of the chloroform filtrate give 8.3 g of pale yellow solid.

The tan and pale yellow solids are combined and re-crystallized from ethanol to give 11.31 g of near-white crystals with melting point 247.5°–249° C. This last crop of crystals is re-crystallized first from 2-propanol and then from methanol-benzene to give 6.06 g of white crystals of 4-[4-[[7-chloro-4-quinolinyl]amino]benzoyl]piperazine of melting point 248.5°–250° C.

Calcd. for $C_{20}H_{19}ClN_4O$: Calcd.: C, 65.48; H, 5.22; N, 15.27; Cl, 9.67. Found: C, 64.60; H, 4.73; N, 14.02; Cl, 9.64.

EXAMPLE 1

(Method A)

In a typical run, 4-[4-[7-trifluoromethylquinolyl]amino]benzoic acid hydrochloride is stirred in dry dimethylformamide (DMF) or dry dimethylsulfoxide (DMSO) under nitrogen gas at room temperature, about 25° C. Between 1.0 and 2.4 molar equivalents of carbonyl diimidazole is added and the mixture is stirred for 1 hour. Usually, 1–2 equivalents of amine is then added. The mixture is stirred further at room temperature (20°–25° C.) for 13–25 hours, poured into aqueous sodium bicarbonate, and extracted with methylene chloride, or when necessary, with 5:3 chloroform-n-butanol. The organic phase is dried over anhydrous sodium sulfate and concentrated in vacuo. The product is either crystallized directly or chromatographed on silica gel with ammonium hydroxide-methanol-methylene chloride and crystallized.

EXAMPLE 2

1-(2-pyridinyl)-4-[4-[7-(trifluoromethyl)quinolinyl]amino]benzoylpiperazine

In the manner given in Example 1, using dimethylsulfoxide as solvent, 1-(2-pyridinyl)piperazine as the amine, and 4-[4-[7-trifluoromethylquinolyl]amino]benzoic acid provides 1-(2-pyridinyl)-4-[4-[[7-(trifluoromethyl)-4-quinolinyl]amino]benzoyl]piperazine in 73% yield and of melting point 251°–252.5° C.

Analysis Calcd. for $C_{26}H_{22}N_5OF_3$: Calcd.: C, 65.40; H, 4.64; N, 14.67. Found: C, 65.01; H, 4.73; N, 14.43.

EXAMPLE 3

1-[2-(4-methylpyridinyl)]-4-[4-[[7-(trifluoromethyl)-quinolinyl]amino]benzoyl]piperazine In the manner given in Example 1, reacting during 20 hours 4-[4-[7-trifluoromethylquinolyl]amino]benzoic acid hydrochloride in dimethylsulfoxide with 1-[2-(4-methylpyridinyl)]piperazine produces 1-[2-(4-methylpyridinyl)]-4-[4-[[7-(trifluoromethyl)quinolinyl]amino]benzoyl]piperazine.

EXAMPLE 4

1-[2-(4-propylpyridinyl)]-4-[4-[[7-(trifluoromethyl)-4-quinolinyl]amino]benzoyl]piperazine In the manner given in Example 1, reacting during 28 hours 4-[4-[7-trifluoromethylquinolyl]amino]benzoic acid hydrochloride in dimethylsulfoxide with 1-[2-(4-propylpyridinyl)]piperazine produces 1-[2-(4-propylpyridinyl)]-4-[4-[[7-(trifluoromethyl)quinolinyl]amino]benzoyl]piperazine.

EXAMPLE 5

1-(2,3,5,6-tetrachloro-4-pyridinyl)-4-[4-[[7-(trifluoromethyl)-4-quinolinyl]amino]benzoyl]piperazine A mixture of 2.42 g 4-[4-[[7-(trifluoromethyl)-4-quinolinyl]amino]benzoyl]piperazine [U.S. Pat. No. 4,025,629] 1.52 g (0.00605 mol) of pentachloropyridine, and 0.84 ml (0.00605 mol) of triethylamine in 20 ml of ethylene glycol are heated at 80° C. for 8 hours. The mixture is partitioned between methylene chloride and aqueous sodium bicarbonate. The organic phase is dried with anhydrous sodium sulfate, concentrated and chromatographed (40–60µ silica gel) with methylene chloride to 2% methanol/½% ammonium hydroxide (methylene chloride) to yield 2.00 g (54%) of 1-(2,3,5,6-tetrachloro-4-pyridinyl)-4-[4-[[7-(trifluoromethyl)-4-quinolinyl]amino]benzoyl]piperazine. This is re-crystallized from methylene chloride to give a crop of 0.94 g of 1-(2,3,5,6-tetrachloro-4-pyridinyl)-4-[4-[[7-(trifluoromethyl)-4-quinolinyl]amino]benzoyl]piperazine (melting point 222°–223.5° C.). The infrared spectrum is consistent with the assigned structure.

EXAMPLE 6

1-(2-pyrazinyl)-4-[4-[[7-(trifluoromethyl)-4-quinolinyl]amino]benzoyl]piperazine A mixture of 2.00 g (0.005 mol) of 4-[4-[[7-(trifluoromethyl)-4-quinolinyl]amino]benzoyl]piperazine [U.S. Pat. No. 4,025,629] 0.57 g (0.005 mol) of 2-chloropyrazine, and 0.505 g (0.005 mol) of triethylamine is heated in 20 ml of ethylene glycol at 75° C. for 24 hours and at 95° C. for 24 hours. The mixture is partitioned with 1 N toluenesulfonic acid in water and methylene chloride. The aqueous phase is made basic and extracted with methylene chloride. The organic phase is dried with anhydrous sodium sulfate and concentrated. The residue is chromatographed (4% methanol/½% ammonium hydroxide/methylene chloride) to yield 0.92 g (38%) of 1-(2-pyrazinyl)-4-[4-[[7-(trifluoromethyl)-4-quinolinyl]amino]benzoyl]piperazine. This is re-crystallized from methylene chloride to give 0.48 g of the pure product of melting point 260°–261° C. The IR spectrum is consistent with the named structure.

EXAMPLE 7

4-(2-pyrimidinyl)-1-[4-[[7-(trifluoromethyl)-4-quinolinyl]amino]benzoyl]piperazine A mixture of 1.30 g (0.0114 mol) of 2-chloropyrimidine, 3.50 g (0.00875 mol) of 1-[4-[[7-(trifluoromethyl)-4-quinolinyl]amino]benzoyl]piperazine, and 1.2 g of triethylamine in 50 ml of ethanol is stirred at 50° C. for 15 hours and at reflux for 8 hours. The mixture is partitioned between methylene chloride and aqueous 1 N sodium hydroxide. The organic phase is dried and concentrated. The residue is re-crystallized from methylene chloride and ethanol to yield 4.00 g of 4-(2- pyrimidinyl)-1-[4-[[7-(trifluoromethyl)-4-quinolinyl]amino]benzoyl]piperazine, of melting point 246°-247.5° C.

Anal. Calcd. for $C_{25}H_{21}N_6OF_3$: Calcd.: C, 62.75; H, 4.42; N, 17.57. Found: C, 62.12; H, 4.63; N, 17.44.

EXAMPLE 8

1-(2-amino-6-methyl-4-pyrimidinyl)-4-[4-[[7-(trifluoromethyl)-4-quinolinyl]amino]benzoyl]piperazine A mixture of 4.00 g (0.010 mol) of 4-[4-[[7-(trifluoromethyl)-4-quinolinyl]amino]benzoyl]piperazine, 1.43 g (0.010 mol) of 2-amino-4-chloro-6-methylpyrimidine, 1.39 ml (0.01 mol) of triethylamine, and 125 ml of ethylene glycol is stirred at 100° C. for 5 hours. The reaction mixture is shaken with aqueous sodium carbonate and methylene chloride and the remaining solid is then collected by filtration. The product, 1-(2-amino-6-methyl-4-pyrimidinyl)-4-[4-[[7-(trifluoromethyl)-4-quinolinyl]amino]benzoyl]piperazine (4.06 g, 80%), is crystallized twice from methanol/methylene chloride; it has a melting point of 283°-286° C.

Anal. Calcd. for $C_{26}H_{24}F_3N_7O$: Calcd.: C, 61.53; H, 4.77; N, 19.32. Found: C, 61.42; H, 4.75; N, 19.34.

EXAMPLE 9

1-(2,6-dimethoxy-4-pyrimidinyl)-4-[4-[[7-(trifluoromethyl)-4-quinolinyl]amino]benzoyl]piperazine A mixture of 3.70 g (0.00924 mol) of 4-[4-[[7-(trifluoromethyl)-4-quinolinyl]amino]benzoyl]piperazine, 1.61 g (0.00924 mol) of 6-chloro-2,4-dimethoxypyrimidine, 1.29 ml (0.00924 mol) of triethylamine and 125 ml of ethylene glycol is heated at 100° C. for 6 hours. After cooling, the precipitated solid is collected on a sintered glass funnel and dried in the air over the weekend. The solid is chromatographed on silica gel, eluting with 6% methanol/methylene chloride, to give 2.15 g (43%) of 1-(2,6-dimethoxy-4-pyrimidinyl)-4-[4-[[7-(trifluoromethyl)-4-quinolinyl]amino]benzoyl]piperazine of melting point 260°-262° C., after crystallization from methanol/methylene chloride.

Anal. Calcd. for $C_{27}H_{25}F_3N_6O_3$: Calcd.: C, 60.22; H, 4.68; N, 15.61. Found: C, 60.27; H, 4.72; N, 15.49.

EXAMPLE 10

1-[2-(methylthio)-4-pyrimidinyl]-4-[4-[[7-(trifluoromethyl)-4-quinolinyl]amino]benzoyl]piperazine A mixture of 1.50 g (0.0037 mol) of 4-[4-[[7-(trifluoromethyl)-4-quinolinyl]amino]benzoyl]piperazine [U.S. Pat. No. 4,025,629], 0.44 ml (0.00375 mol) of 4-chloro-2-methylthiopyrimidine, 0.52 ml (0.00375 mol) of triethylamine, and 125 ml of ethanol is stirred at reflux for 3 hours. After cooling, the ethanol is removed in vacuo and the residue is stirred with methylene chloride and aqueous sodium bicarbonate. The resultant solid is collected and washed with water and ether. Crystallization from methanol-chloroform gives 0.52 g (26%) of 1-[2-(methylthio)-4-pyrimidinyl]-4-[4-[[7-(trifluoromethyl)-4-quinolinyl]amino]benzoyl]piperazine, of melting point 166°-267° C.

Anal. Calcd. for $C_{26}H_{23}F_3N_6OS$: Calcd.: C, 59.53; H, 4.42; N, 16.02. Found: C, 59.78; H, 4.52; N, 15.95.

EXAMPLE 11

1-(3-methoxypyrazin-2-yl)-4-[4-[[7-(trifluoromethyl)-4-quinolinyl]amino]benzoyl]piperazine In the manner given in Example 6, a mixture of 4-[4-[[7-(trifluoromethyl)-4-quinolinyl]amino]benzoyl]piperazine, 2-chloro-3-methoxypyrazine and triethylamine is heated in ethylene glycol at 75° to 95° C. to give 1-(3-methoxypyrazin-2-yl)-4-[4-[[7-(trifluoromethyl)-4-quinolinyl]amino]benzoyl]piperazine.

EXAMPLE 12

1-(3-methylpyrazin-2-yl)-4-[4-[[7-(trifluoromethyl)-4-quinolinyl]amino]benzoyl]piperazine In the manner given in Example 6, a mixture of 4-[4-[[7-(trifluoromethyl)-4-quinolinyl]amino]benzoyl]piperazine, 2-chloro-3-methylpyrazine and triethylamine is heated in ethylene glycol at 75° to 95° C. to give 1-(3-methylpyrazin-2-yl)-4-[4-[[7-(trifluoromethyl)-4-quinolinyl]amino]benzoyl]piperazine.

EXAMPLE 13

1-(2-methoxypyridin-4-yl)-4-[4-[[7-(trifluoromethyl)-4-quinolinyl]amino]benzoyl]piperazine In the manner given in Example 5, a mixture of 4-[4-[[7-(trifluoromethyl)-4-quinolinyl]amino]benzoyl]piperazine, 4-chloro-2-methoxypyridine and triethylamine is heated in ethylene glycol at 80° C. to give 1-(2-methoxypyridin-4-yl)-4-[4-[[7-(trifluoromethyl)-4-quinolinyl]amino]benzoyl]piperazine.

EXAMPLE 14

1-[(dimethylamino)sulfonyl]-4-[4-[[7-(trifluoromethyl)-4-quinolinyl]amino]benzoyl]piperazine Dimethylsulfamoyl chloride (0.72 g, 0.54 ml, 0.005 mol) is added dropwise to a solution of 2.00 g (0.005 mol) of 4-[4-[[7-(trifluoromethyl)-4-quinolinyl]amino]benzoyl]piperazine and 2 ml of triethylamine in 20 ml of dimethylformamide. The reaction is stirred for 19 hours and then partitioned with chloroform-aqueous sodium carbonate. The organic phase is dried over anhydrous sodium sulfate, concentrated, and chromatographed with methylene chloride to 1% methanol/chloroform on silica gel to give 2.24 g of 1-[(dimethylamino)sulfonyl]-4-[4-[[7-(trifluoromethyl)-4-quinolinyl]amino]benzoyl]piperazine. This is crystallized from methylene chloride-cyclohexane to give 1.60 g of 1-[(dimethylamino)sulfonyl]-4-[4-[[-7-(trifluoromethyl)-4-quinolinyl]amino]benzoyl]piperazine of melting point 223°-224.5° C.

Anal. Calcd. for $C_{23}H_{24}N_5O_3F_3S$: Calcd. C, 54.43; H, 4.77; N, 13.80. Found C, 54.38; H, 5.11; N, 13.91.

EXAMPLE 15

1-[(4-methylphenyl)sulfonyl]-4-[4-[[7-(trifluoromethyl)-4-quinolinyl]amino]benzoyl]piperazine To a suspension of 4-[4-[[7-(trifluoromethyl)-4-quinolinyl]amino]benzoyl]piperazine (2 g, 0.005 mol) in 20 ml of tetrahydrofuran and 0.5 ml of triethylamine is added a solution of p-toluenesulfonyl chloride (0.95 g, 0.005 mol) in 10 ml of tetrahydrofuran dropwise over a 15 minute period, under nitrogen. After complete addition, the resultant solution is stirred at room temperature for 1 hour. This is quenched in cold water and extracted with methylene chloride (2×, 50 ml). The methylene chloride solution is washed with water, saturated sodium chloride solution, dried over anhydrous sodium sulfate, and concentrated to a yellow solid. This, after re-crystallization from methanol, gives 2.5 g (90%) of white crystalline 1-[(4-methylphenyl)sulfonyl]-4-[4-[[7-(trifluoromethyl)-4-quinolinyl]amino]benzoyl]piperazine with melting point 215°-217° C.

Anal. Calcd. for $C_{26}H_{25}F_3N_4SO_3$: Calcd. C, 60.63; H, 4.55; N, 10.10; S, 5.77. Found C, 60.81; H, 4.54; N, 10.12; S, 6.00.

EXAMPLE 16

1-[(4-chlorophenyl)sulfonyl]4-[4-[[7-(trifluoromethyl)-4-quinolinyl]amino]benzoyl]piperazine In the manner given in Example 15, 4-[4-[[7-(trifluoromethyl)-4-quinolinyl]amino]benzoyl]piperazine is reacted with 4-chlorophenylsulfonyl chloride in the presence of triethylamine under nitrogen to give 1-[(4-chlorophenyl)sulfonyl]-4-[4-[[7-(trifluoromethyl)-4-quinolinyl]amino]benzoyl]piperazine of melting point 234°–236° C. in 77% yield.

Anal. Calcd. for $C_{27}H_{22}ClF_3N_4SO_3$: Calcd. C, 56.40; H, 3.86; N, 9.75; Cl, 6.17; F, 9.91; S, 5.57. Found C, 56.31; H, 3.80; N, 9.58; Cl, 6.49; F, 9.85; S, 5.72.

EXAMPLE 17

1[(4-fluorophenyl)sulfonyl]-4-[4-[[7-(trifluoromethyl)-4-quinolinyl]amino]benzoyl]piperazine To a suspension of 4-[4-[[7-(trifluoromethyl)-4-quinolinyl]amino]benzoyl]piperazine (2 g, 0.005 mol) and 0.5 g of triethylamine in 30 ml of tetrahydrofuran is added dropwise a solution of p-fluorophenylsulfonyl chloride in 10 ml of tetrahydrofuran over a 15 minute period. After complete addition, the resultant mixture is stirred for 1 hour at room temperature. The resulting mixture is filtered and the white solid is washed with more tetrahydrofuran and dried. This is re-crystallized from methanol/methylene chloride to give 2.5 g (92%) of white crystalline 1-[(4-fluorophenyl)sulfonyl]-4-[4-[[7-(trifluoromethyl)-4-quinolinyl]amino]benzoyl]piperazine of melting point 251°–253° C.

Anal. Calcd. for $C_{26}H_{22}F_4N_4SO_3$: Calcd. C, 58.06; H, 3.97; N, 10.03; F, 13.61; S, 5.73. Found C, 58.10; H, 3.98; N, 10.08; F, 13.56; S, 5.91.

EXAMPLE 18

1-[(3-bromophenyl)sulfonyl]-4-[4-[[7-(trifluoromethyl)-4-quinolinyl]amino]benzoyl]piperazine In the manner given in Example 15, 4-[4-[[7-(trifluoromethyl)-4-quinolinyl]amino]benzoyl]piperazine is reacted with 3-bromophenylsulfonyl chloride, in the presence of triethylamine to give 1-[(3-bromophenyl)sulfonyl]-4-[4-[[7-(trifluoromethyl)-4-quinolinyl]amino]benzoyl]piperazine.

EXAMPLE 19

1-[(diethylamino)sulfonyl]-4-[4-[[7-(trifluoromethyl)-4-quinolinyl]amino]benzoyl]piperazine In the manner given in Example 14, 4-[4-[[7-(trifluoromethyl)-4-quinolinyl]amino]benzoyl]piperazine is reacted with diethylsulfamoyl chloride, in the presence of triethylamine to give 1-[(diethylamino)sulfonyl]-4-[4-[[7-(trifluoromethyl)-4-quinolinyl]amino]benzoyl]piperazine.

EXAMPLE 20

1-[(4-trifluoromethylphenyl)sulfonyl]-4-[4-[[7-(trifluoromethyl)-4-quinolinyl]amino]benzoyl]piperazine In the manner given in Example 15, 4-[4-[[7-(trifluoromethyl)phenyl-4-quinolinyl]amino]benzoyl]piperazine is reacted with p-trifluoromethylphenylsulfonyl chloride in the presence of triethylamine to give 1-[4-(trifluoromethyl)phenylsulfonyl]-4-[4-[[7-(trifluoromethyl)-4-quinolinyl]amino]benzoyl]piperazine.

EXAMPLE 21

1-[(4-methoxyphenyl)sulfonyl]-4-[4-[[7-(trifluoromethyl)-4-quinolinyl]amino]benzoyl]piperazine In the manner given in Example 15, 4-[4-[[7-(trifluoromethyl)-4-quinolinyl]amino]benzoyl]piperazine is reacted with 4-methoxyphenylsulfonyl chloride, in the presence of triethylamine to give 1-[(4-methoxyphenyl)sulfonyl]-4-[4-[[7-(trifluoromethyl)-4-quinolinyl]amino]benzoyl]piperazine of melting point 221°–223° C. in a 53% yield.

Anal. Calcd. for $C_{28}H_{25}F_3N_4SO_4$: Calcd. C, 58.94; H, 4.42; N, 9.82; F, 9.99; S, 5.61. Found C, 58.99; H, 4.46; N, 9.90; F, 9.93; S, 5.81.

EXAMPLE 22

1-[(2,4-diethylphenyl)sulfonyl]-4-[4-[[7-(trifluoromethyl)-4-quinolinyl]amino]benzoyl]piperazine In the manner given in Example 15, 4-[4-[[7-(trifluoromethyl)-4-quinolinyl]amino]benzoyl]piperazine is reacted with 2,4-diethylphenylsulfonyl chloride, in the presence of triethylamine to give 1-[(2,4-diethylphenyl)sulfonyl]-4-[4-[[7-(trifluoromethyl)-4-quinolinyl]amino]benzoyl]piperazine.

EXAMPLE 23

1-[[(3-chlorophenyl)amino]carbonyl]-4-[4-[[7-(trifluoromethyl)-4-quinolinyl]amino]benzoyl]piperazine To a suspension of 4-[4-[[7-(trifluoromethyl)-4-quinolinyl]amino]benzoyl]piperazine (2.0 g, 0.005 mol) in 15 ml of methylene chloride is added a solution of m-chlorophenyl isocyanate in 10 ml of methylene chloride at 0° C. under nitrogen. The resulting suspension is stirred for 1 hour at room temperature. The above mixture is then filtered and the white solid residue is washed with more methylene chloride and dried. This is recrystallized from methanol/methylene chloride to give 2.5 g (90%) of white crystalline 1-[[(3-chlorophenyl)amino]carbonyl]-4-[4-[[7-(trifluoromethyl)-4-quinolinyl]amino]benzoyl]piperazine of melting point 266°–268° C.

Anal. Calcd. for $C_{28}H_{23}ClF_3N_5O_2$: Calcd. C, 60.71; H, 4.18; N, 12.65; Cl, 6.40; F, 10.29. Found C, 60.35; H, 4.20; N, 12.42; Cl, 6.39; F, 10.24.

EXAMPLE 24

N-[(4-methylphenyl)sulfonyl]-4-[4-[[7-trifluoromethyl)-4-quinolinyl]amino]benzoyl]piperazine-1-carboxamide To a suspension of 4-[4-[[7-(trifluoromethyl)-4-quinolinyl]amino]benzoyl]piperazine (2 g, 0.005 mol) in 15 ml of methylene chloride under nitrogen is added dropwise a solution of p-tolylsulfonyl-isocyanate in 10 ml of methylene chloride over a period of 10 minutes. After complete addition, the resultant suspension is stirred at room temperature for 1 hour. The white solid is filtered, washed with more methylene chloride, and dried giving 2.6 g (87%) of N-[(4-methylphenyl)sulfonyl]-4-[4-[[7-(trifluoromethyl)-4-quinolinyl]amino]benzoyl]piperazine-1-carboxamide of melting point 253°–255° C. Infrared and mass spectra are consistent with the assigned structure.

EXAMPLE 25

1-[[[3-(trifluoromethyl)phenyl]amino]carbonyl]-4-[4-[[7-(trifluoromethyl)-4-quinolinyl]amino]benzyl]piperazine To a suspension of 4-[4-[[7-(trifluoromethyl)-4-quinolinyl]amino]benzoyl]piperazine (2 g, 0.005 mol) in 15 ml of methylene chloride is added dropwise a solution of m-trifluoromethylphenyl isocyanate (0.935 g, 0.005 mol) in 10 ml of methylene chloride under nitrogen at room temperature. After complete addition, the resultant suspension is stirred at room temperature for 1 hour. This is then filtered and the white residue which is precipitated is washed with methylene chloride and dried. This is re-crystallized from methanol to give 2 g (68%) of white crystalline 1-[[[3-(trifluoromethyl)phenyl]amino]carbonyl]-4-[4-[[7-(trifluoromethyl)-4-quinolinyl]amino]benzyl]piperazine of melting point 198°-200° C.

Anal. Calcd. for $C_{29}H_{23}F_6N_5O_2$: Calcd. C, 59.28; H, 3.95; N, 11.92; F, 19.40. Found C, 59.43; H, 4.07; N, 11.92; F, 19.37.

EXAMPLE 26

1-[[(4-methylphenyl)amino]carbonyl]-4-[4-[[7-(trifluoromethyl)-4-quinolinyl]-amino]benzoyl]piperazine To a suspension of 4-[4-[[7-(trifluoromethyl)-4-quinolinyl]amino]benzoyl]piperazine (2 g, 0.005 mol) in 15 ml of methylene chloride is added dropwise a solution of p-tolyl isocyanate in 10 ml of methylene chloride under nitrogen at room temperature. After complete addition, the resultant suspension is stirred at room temperature for 2 hours. This suspension is then filtered and the white residue is washed with methylene chloride and dried. This is re-crystallized from methanol/methylene chloride to give 2.5 g (93%) of white crystalline 1-[[(4-methylphenyl)amino]carbonyl]-4-[4-[[7-(trifluoromethyl)-4-quinolinyl]amino]benzoyl]piperazine of melting point 280°-282° C.

Anal. Calcd. for $C_{29}C_{26}F_3N_5O_2$: Calcd. C, 65.28; H, 4.91; F, 13.13; F, 10.68. Found C, 65.46; H, 4.82; N, 13.07; F, 10.50.

EXAMPLE 27

1-[[(3-fluorophenyl)amino]carbonyl]-4-[4-[[7-trifluoromethyl)-4-quinolinyl]amino]benzoyl]piperazine In the manner given in Example 23, 4-[4-[[7-(trifluoromethyl)-4-quinolinyl]amino]benzoyl]piperazine is reacted with m-fluorophenyl isocyanate to give 1-[[(3-fluorophenyl)amino]carbonyl]-4-[4-[[(7-trifluoromethyl)-4-quinolinyl]amino]benzoyl]piperazine.

EXAMPLE 28

1-[[(4-fluorophenyl)amino]carbonyl]-4-[4-[[(7-trifluoromethyl)-4-quinolinyl]amino]benzoyl]piperazine.

In the manner given in Example 23, 4-[4-[[7-(trifluoromethyl)-4-quinolinyl]amino]benzoyl]piperazine is reacted with p-fluorophenyl isocyanate to give 1-[[(4-fluorophenyl)amino]carbonyl]-4-[4-[[(7-trifluoromethyl)-4-quinolinyl]amino]benzoyl]piperazine.

EXAMPLE 29

1-[[(2-bromophenyl)amino]carbonyl]-4-[4-[[7-chloro-4-quinolinyl]amino]benzoyl]piperazine.

In the manner given in Example 23, 4-[4-[[7-chloro-4-quinolinyl]amino]benzoyl]piperazine is reacted with o-bromophenyl isocyanate to give 1-[[(2-bromophenyl)amino]carbonyl]-4-[4-[[7-chloro-4-quinolinyl]amino]benzoyl]piperazine.

EXAMPLE 30

1-[[(4-ethylphenyl)amino]carbonyl]-4-[4-[[(7-chloro)-4-quinolinyl]amino]benzoyl]piperazine In the manner given in Example 23, 4-[4-[[7-(chloro)-4-quinolinyl]amino]benzoyl]piperazine is reacted with p-ethylphenyl isocyanate to give 1-[[(4-ethylphenyl)amino]carbonyl]-4-[4-[[(7-chloro)-4-quinolinyl]amino]benzoyl]piperazine.

EXAMPLE 31

1-[[(3-chlorophenyl)amino]carbonyl]-4-[4-[[(7-chloro)-4-quinolinyl]amino]benzoyl]piperazine In the manner given in Example 23, 4-[4-[[7-(chloro)-4-quinolinyl]amino]benzoyl]piperazine is reacted with m-chlorophenyl isocyanate to give 1-[[(3-chlorophenyl)amino]carbonyl]-4-[4-[[(7-chloro)-4-quinolinyl]amino]benzoyl]piperazine.

EXAMPLE 32

1-[[4-methoxyphenyl)amino]carbonyl]-4-[4-[[(7-trifluoromethyl)-4-quinolinyl]amino]benzoyl]piperazine.

In the manner given in Example 23, 4-[4-[[7-(trifluoromethyl)-4-quinolinyl]amino]benzoyl]piperazine is reacted with p-methoxyphenyl isocyanate to give 1-[[(4-methoxyphenyl)amino]carbonyl]-4-[4-[[(7-trifluoromethyl)-4-quinolinyl]amino]benzoyl]piperazine.

EXAMPLE 33

1-[2-(4-ethyl-6-methylthio)triazinyl]-4-[4-[[7-(trifluoromethyl)-4-quinolinyl]amino]benzoyl]piperazine In the manner givein in Example 10, 4-[4-[[[7-(trifluoromethyl)-4-quinolinyl]amino]benzoyl]piperazine is reacted with (2-chloro-4-ethyl-6-methylthio)triazine to give 1-[2-(4-ethyl-6-methylthio)triazinyl]-4-[4-[[7-(trifluoromethyl)-4-quinolinyl]amino]benzoyl]piperazine.

EXAMPLE 34

1-[2-(4-diethylamino)triazinyl]-4-[4-[[7-(trifluoromethyl)-4-quinolinyl]amino]benzoyl]piperazine In the manner given in Example 8, 4-[4-[[7-(trifluoromethyl)-4-quinolinyl]amino]benzoyl]piperazine is reacted with (2-bromo-4-diethylamino)triazine to give 1-[2-(4-diethylamino)triazinyl]-4-[4-[[7-(trifluoromethyl)-4-quinolinyl]amino]benzoyl]piperazine.

EXAMPLE 35

1-[2-(5-propylthio)piperazinyl]-4-[4-[[7-(trifluoromethyl)-4-quinolinyl]amino]benzoyl]piperazine In the manner given in Example 10, 4-[4-[[7-(trifluoromethyl)-4-quinolinyl]amino]benzoyl]piperazine is reacted with (2-chloro-5-propylthio)pyrazine to give 1-[2-(5-propylthio)pyrazinyl]-4-[4-[[7-(trifluoromethyl)-4-quinolinyl]amino]benzoyl]piperazine.

EXAMPLE 36

1-[2-(3-dimethylamino)pyrazinyl]-4-[4-[[7-(trifluoromethyl)-4-quinolinyl]amino]benzoyl]piperazine In the manner given in Example 8, 4-[4-[[7-(trifluoromethyl)-4-quinolinyl]amino]benzoyl]piperazine is reacted with (2-chloro-3-dimethylamino)pyrazine to give 1-[2-(3-dimethylamino)pyrazinyl]-4-[4-[[7-(trifluoromethyl)-4-quinolinyl]amino]benzoyl]piperazine.

In the manner given in Example 1 to 4, other 1-(2-pyridinyl)-4-[4-[[7-(trifluoromethyl) or 7-(chloro)-4-quinolinyl]amino]benzoyl]piperazines can be made by reacting a 4-[4-[7-(trifluoromethyl) or 7-(chloro)-quinolinyl]amino]benzoic acid hydrochloride with carbonyl diimidazole and a selected 1-(2-pyridinyl)piperazine. Representative compounds thus produced include:

1-(2-pyridinyl)-4-[4-[[7-chloro-4-quinolinyl]amino]benzoyl]piperazine
1-[2-(4-methylpyridinyl)]-4-[[7-chloro-4-quinolinyl]amino]benzoyl]piperazine
1-[2-(3-ethylpyridinyl)]-4-[4-[[7-chloro-4-quinolinyl]amino]benzoyl]piperazine
1-[2-(4-ethylpyridinyl)]-4-[4-[[7-(trifluoromethyl)-4-quinolinyl]amino]benzoyl]piperazine
1-[2-(4-propylpyridinyl)]-4-[4-[[7-chloro-4-quinolinyl]amino]benzoyl]piperazine
1-[2-(4-dimethylaminopyridinyl)]-4-[4-[[7-(trifluoromethyl)-4-quinolinyl]amino]benzoyl]piperazine
1-[2-(4-thiomethylpyridinyl)]-4-[4-[[7-(trifluoromethyl)-4-quinolinyl]amino]benzoyl]piperazine
1-[2-(4-chloropyridinyl)]-4-[4-[[7-(trifluoromethyl)-4-quinolinyl]amino]benzoyl]piperazine
1-[2-(4,6-dichloropyridinyl)]-4-[4-[[7-(trifluoromethyl)-4-quinolinyl]amino]benzoyl]piperazine
1-[2-(4,6-dimethylpyridinyl)]-4-[4-[[7-chloro-4-quinolinyl]amino]benzoyl]piperazine
1-[2-(3-bromo)pyridinyl]-4-[[7-(trifluoromethyl)-4-quinolinyl]amino]benzoyl]piperazine
1-[2-(4-methoxy)pyridinyl]-4-[4-[[7-(trifluoromethyl)-4-quinolinyl]amino]benzoyl]piperazine
1-[2-(4-bromo-6-methoxy)pyridinyl]-4-[4-[[7-(trifluoromethyl)-4-quinolinyl]amino]benzoyl]piperazine
1-[2-(4-trifluoromethyl)pyridinyl]-4-[4-[[7-(trifluoromethyl)-4-quinolinyl]amino]benzoyl]piperazine
1-[2-(4-ethoxy)pyridinyl]-4-[4-[[7-(trifluoromethyl)-4-quinolinyl]amino]benzoyl]piperazine
1-[2-[4,6-bis(methylthio)]pyridinyl]-4-[4-[[7-(trifluoromethyl)-4-quinolinyl]amino]benzoy Similarly the corresponding 7-chloro compounds can be prepared.

In the manner given in Examples 5 through 13, other substituted pyridinyl, triazinyl, pyrazinyl- or pyrimidinyl- 4-[[7-(trifluoromethyl or chloro)quinolinyl]amino]benzoyl piperazines can be prepared from haloheterocyclic aromatic compounds and 4-[4-[[(7-chloro) or (7-trifluoromethyl) 4-quinolinyl]amino]benzoyl]piperazines. Representative compounds thus prepared include:

1-(2,3,5,6-tetrabromo-4-pyridinyl)-4-[4-[[(7-chloro)-4-quinolinyl]amino]benzoyl]piperazine
1-(2,5-dimethyl-4-pyridinyl)-4-[4-[[(7-chloro)-4-quinolinyl]amino]benzoyl]piperazine
1-(2-pyrazinyl)-4-[4-[[7-chloro-4-quinolinyl]amino]benzoyl]piperazine
1-[2-(3-methylpyrazinyl)]-4-[4-[[7-chloro-4-quinolinyl]amino]benzoyl]piperazine
1-[2-(3-methoxy)pyrazinyl]-4-[4-[[7-chloro-4-quinolinyl]amino]benzoyl]piperazine
4-(2-pyrimidinyl)-4-[4-[[7-chloro-4-quinolinyl]amino]benzoyl]piperazine
4-[2-(3-methylpyrimidinyl)]-4-[4-[[7-chloro-4-quinolinyl]amino]benzoyl]piperazine
1-[2-chloro-4-pyrimidinyl]-4-[4-[[7-chloro-4-quinolinyl]amino]benzoyl]piperazine
1-[2-(3,5-dimethylpyrazinyl)]-4-[4-[[7-(trifluoromethyl)-4-quinolinyl]amino]benzoyl]piperazine
1-[2-(3,5-dimethoxypyrazinyl)]-4-[4-[[7-(trifluoromethyl)-4-quinolinyl]amino]benzoyl]piperazine
1-[2-(3-methylthiopyrazinyl)]-4-[4-[[7-(trifluoromethyl)-4-quinolinyl]amino]benzoyl]piperazine
1-[2-(5-chloropyrazinyl)]-4-[4-[[7-(trifluoromethyl)-4-quinolinyl]amino]benzoyl]piperazine
1-(2,5-dimethyl-4-pyridinyl)-4-[4-[[7-(trifluoromethyl)-4-quinolinyl]amino]benzoyl]piperazine
1-[2-(5-dimethylaminopyrazinyl)]-4-[4-[[7-(trifluoromethyl)-4-quinolinyl]amino]benzoyl]piperazine
1-[2-(3-bromopyrazinyl)]-4-[4-[[7-(trifluoromethyl)-4-quinolinyl]amino]benzoyl]piperazine
1-[2-(3-ethoxy-5-fluoro)pyrazinyl]-4-[4-[[7-(trifluoromethyl)-4-quinolinyl]amino]benzoyl]piperazine
1-[2-(4-dimethylamino)pyrimidinyl]-4-[4-[[7-(trifluoromethyl)-4-quinolinyl]amino]benzoyl]piperazine
1-[2-(4-ethyl)triazinyl]-4-[4-[[7-chloro-4-quinolinyl]amino]benzoyl]piperazine
1-[2-(4-chloro-6-methyl)triazinyl]-4-[4-[[7-(trifluoromethyl)-4-quinolinyl]amino]benzoyl]piperazine
1-(2-triazinyl)-4-[4-[[7-chloro-4-quinolinyl]amino]benzoyl]piperazine In the manner given in Examples 14 to 22, other 1-(substituted sulfonyl)-4-[4-[[7-chloro or trifluoromethyl)-4-quinolinyl amino]benzoyl]piperazines are prepared by reacting 4-[4-[[7-(chloro or trifluoromethyl)-4-quinolinyl]amino]benzoyl]piperazines with the appropriate sulfonyl chloride or sulfamoyl chloride:

1-[(2-chlorophenyl)sulfonyl]-4-[4-[[7-(trifluoromethyl)-4-quinolinyl]amino]benzoyl]piperazine
1-[(2-fluorophenyl)sulfonyl]-4-[4-[[7-(trifluoromethyl)-4-quinolinyl]amino]benzoyl]piperazine
1-[(4-chlorophenyl)sulfonyl]-4-[4-[[7-chloro-4-quinolinyl]amino]benzoyl]piperazine
1-[(4-fluorophenyl)sulfonyl]-4-[4-[[7-chloro-4-quinolinyl]amino]benzoyl]piperazine
1-[(3-bromophenyl)sulfonyl]-4-[4-[[7-chloro-4-quinolinyl]amino]benzoyl]piperazine
1-[dimethylaminosulfonyl]-4-[4-[[7-chloro-4-quinolinyl]amino]benzoyl]piperazine
1-[4-(trifluoromethyl)phenylsulfonyl]-4-[4-[[7-chloro-4-quinolinyl]amino]benzoyl]piperazine
1-[(4-methoxyphenyl)sulfonyl]-4-[4-[[7-(trifluoromethyl)-4-quinolinyl]amino]benzoyl]piperazine
1-[(4-ethoxyphenyl)sulfonyl]-4-[4-[[7-chloro-4-quinolinyl]amino]benzoyl]piperazine
1-[(4-bromophenyl)sulfonyl]-4-[4-[[7-chloro-4-quinolinyl]amino]benzoyl]piperazine
1-[(2,4-difluorophenyl)sulfonyl]-4-[4-[[7-(trifluoromethyl)-4-quinolinyl]amino]benzoyl]piperazine
1-[dimethylaminosulfonyl]-4-[4-[[7-chloro-4-quinolinyl]amino]benzoyl]piperazine
1-[[3-(trifluoromethyl)phenyl]sulfonyl]-4-[4-[[7-chloro-4-quinolinyl]amino]benzoyl]piperazine
1-[(3,5-dimethoxyphenyl)sulfonyl]-4-[4-[[7-(trifluoromethyl)-4-quinolinyl]amino]benzoyl]piperazine
1-[(3-methoxyphenyl)sulfonyl]-4-[4-[[7-chloro-4-quinolinyl]amino]benzoyl]piperazine
1-(phenylsulfonyl)-4-[4-[[7-chloro-4-quinolinyl]amino]benzoyl]piperazine
1-(phenylsulfonyl)-4-[4-[[7-(trifluoromethyl)-4-quinolinyl]amino]benzoyl]piperazine; and the like.

In the manner given in Examples 23 through 32, other 1-[[unsubstituted amino]carbonyl]-4-[4-[[7-(chloro or trifluoromethyl)-4-quinolinyl]amino]benzoyl]piperazines are prepared by reacting 4-[4-[[7-(trifluoromethyl or chloro)-4-quinolinyl]amino]benzoyl]piperazine with a selected isocyanate. Representative compounds thus produced include:

1-[[(4-bromophenyl)amino]carbonyl]-4-[4-[[7-(trifluoromethyl)-4-quinolinyl]amino]benzoyl]piperazine 1-[[(4-trifluoromethylphenyl)amino]carbonyl]-4-[4-[[7-(trifluoromethyl)-4-quinolinyl]amino]benzoyl]piperazine 1-[[(4-ethylphenyl)amino]carbonyl]-4-[4-[[7-(trifluoromethyl)-4-quinolinyl]amino]benzoyl]piperazine 1-[[(3-propoxyphenyl)amino]carbonyl]-4-[4-[[7-(trifluoromethyl)-4-quinolinyl]amino]benzoyl]piperazine 1-[[(4-chloro-6-ethylphenyl]amino]carbonyl]-4-[4-[[7-chloro-4-quinolinyl]amino]benzoyl]piperazine 1-[[(2,4-dibromophenyl)amino]carbonyl]-4-[4-[[7-chloro-4-quinolinyl]amino]benzoyl]piperazine and the like.

The pharmacologically acceptable acid addition salts of compounds of formula II (as well as of formulae IIA and IIB) can be prepared and isolated by conventional processes, such as reacting a compound of formula II with a selected pharmacologically acceptable acid. Such acids include hydrochloric, hydrobromic, phosphoric, sulfuric, acetic, tartaric, lactic, pamoic, citric, malic, maleic, methanesulfonic, benzenesulfonic, cyclohexanesulfamic acids, toluenesulfonic, and the like. The reaction is conveniently performed in an organic solvent, e.g., ether, dioxane or tetrahydrofuran, ethanol, methanol, ethyl acetate; the salts can be recovered by crystallization, precipitation or evaporating the solvent. These salts are useful in the same manner as the free base.

The following Examples set forth illustrative formulations which are useful for the practice of this invention:

EXAMPLE 37

One thousand tablets for oral use, each containing 50 mg of 1-[[(3-chlorophenyl)amino]carbonyl]-4-[4-[[7-(trifluoromethyl)-4-quinolinyl]amino]benzoyl]piperazine as essential active ingredient are prepared from the following ingredients:

| Essential active ingredient | 50 g |
|---|---|
| Dicalcium phosphate | 150 g |
| Methylecellulose, U.S.P. (15 cups) | 6.5 g |
| Talc | 20 g |
| Calcium stearate | 2.5 g |

The essential active ingredient and dicalcium phosphate are mixed well, granulated with 7.5% aqueous solution of methylcellulose, passed through a No. 8 screen and dried carefully. The dried granules are passed through a No. 12 screen, mixed with the talc and stearate and compressed into tablets. These tablets are useful in the treatment of severe hypertension in adult humans at a dose of 1 tablet 2 or 3 times a day.

EXAMPLE 38

One thousand two-piece hard gelatin capsules for oral use, each capsule containing 75 mg of 1-[(4-methylphenyl)sulfonyl]-4-[4-[[7-(trifluoromethyl)-4-quinolinyl]amino]benzoyl]piperazine as the essential active ingredient are prepared from the following ingredients:

| Essential active ingredient | 75 g |
|---|---|
| Lactose, U.S.P. | 100 g |
| Starch, U.S.P. | 10 g |
| Talc, U.S.P. | 5 g |
| Calcium stearate | 1 g |

The finely powdered materials are mixed thoroughly, then filled into hard gelatin capsules of appropriate size.

A satisfactory clinical response is obtained in adults showing hypertension with 1 capsule 4 times a day.

EXAMPLE 39

One-piece soft elastic capsules for oral use, each containing 10 mg of 1-[(4-fluorophenyl)sulfonyl]-4-[4-[[7-(trifluoromethyl)-4-quinolinyl]amino]benzoyl]piperazine as essential active ingredient are prepared in the usual manner by first dispersing the powdered active material in sufficient corn oil to render the material capsulatable.

One capsule 4 times a day is useful in the treatment of moderate hypertension in adult humans.

EXAMPLE 40

An aqueous oral preparation containing in each teaspoonful (5 ml) 15 mg of 1-[(4-chlorophenyl)sulfonyl]-4-[4-[[7-(trifluoromethyl)-4-quinolinyl]amino]benzoyl]piperazine as essential active ingredient is prepared from the following ingredients:

| Essential active ingredient hydrochloride | 30 g |
|---|---|
| Methylparaben, U.S.P. | 7.5 g |
| Propylparaben, U.S.P. | 2.5 g |
| Saccharin sodium | 12.5 g |
| Cyclamate sodium | 2.5 g |
| Glycerin | 3000 ml |
| Tragacanth powder | 10 g |
| Orange oil flavor | 10 g |
| F.D. and C. Orange dye | 7.5 g |
| Deionized water, q.s. to | 10,000 ml |

The foregoing aqueous preparation is useful in the treatment of adult hypertension at a dose of 1 teaspoonful 4 times a day.

EXAMPLE 41

One thousand tablets for oral administration, each containing 5 mg of 1-[(4-fluorophenyl)sulfonyl]-4-[4-[[7-(trifluoromethyl)-4-quinolinyl]amino]benzoyl]piperazine as active ingredient, is prepared from:

| Essential active ingredient, micronized | 5 g |
|---|---|
| Phenobarbital | 16.2 g |
| Lactose | 150 g |
| Starch | 15 g |
| Magnesium stearate | 1.5 g |

The ingredients are thoroughly mixed and slugged. The slugs are broken down by forcing through a screen and the resulting granules are then compressed into tablets.

These tablets are useful in treating hypertensive dogs at a dose of 1 to 3 tablets depending on the weight of the animal and its condition.

EXAMPLE 42

A sterile aqueous suspension suitable for intramuscular injection and containing in each milliliter, 9 mg of 1-[(4-fluorophenyl)sulfonyl]-4-[4-[[7-(trifluoromethyl)-4-quinolinyl]amino]benzoyl]piperazine as essential active ingredient is prepared from the following ingredients:

| Essential active ingredient hydrochloride | 9.5 g |
|---|---|
| Polyethylene glycol 4000, U.S.P. | 3 g |
| Sodium chloride | 0.9 g |
| Polysorbate 80, U.S.P. | 0.4 g |
| Sodium metabisulfite | 0.1 g |
| Methylparaben, U.S.P. | 0.18 g |
| Propylparaben, U.S.P. | 0.02 g |
| Water for injection, q.s. to | 1000 ml |

The preceding sterile injectable is useful in the treatment of hypertension in children at a dose of 1 or 2 ml.

EXAMPLE 43

One thousand suppositories, each weighing 2.5 g and containing 100 mg of 1-(2,3,5,6-tetrachloro-4-pyridinyl)-4-[4-[[7-(trifluoromethyl)-4-quinolinyl]amino]benzoyl]piperazine as essential active ingredient are prepared from the following ingredients:

| Essential active ingredient | 100 g |
|---|---|
| Propylene glycol | 165 g |
| Polyethylene glycol 4000 g.s. | 2500 g |

The essential active ingredient is added to the propylene glycol and the mixture milled until uniformly dispersed. The PEG 4000 is melted and the propylene glycol dispersion added. The suspension is poured into molds and allowed to cool and solidify.

These suppositories are useful in the treatment of moderate hypertension at a dose of 1 suppository rectally three times a day.

EXAMPLE 44

One thousand hard gelatin capsules for oral use, each containing 10 mg of 1-[(4-fluorophenyl)sulfonyl]-4-[4-[[7-(trifluoromethyl)-4-quinolinyl]amino]benzoyl]piperazine as essential active ingredient and 25 mg of hydrochlorothiazide are prepared from the following ingredients:

| Essential active ingredient, micronized | 10 g |
|---|---|
| Hydrochlorothiazide | 25 g |
| Starch | 125 g |
| Talc | 25 g |
| Magnesium stearate | 1.5 g |

One capsule 4 times a day is useful in the relief of moderate hypertension in adult humans.

EXAMPLE 45

Ten thousand scored tablets for oral use, each containing 25 mg of 1-[(4-fluorophenyl)sulfonyl]-4-[4-[[7-(trifluoromethyl)-4-quinolinyl]amino]benzoyl]piperazine as essential active ingredient and 0.08 mg of reserpine, are prepared from the following ingredients and using the procedure of Example 41.

| Essential active ingredient, micronized | 250 g |
|---|---|
| Reserpine | 0.8 g |
| Lactose | 1500 g |
| Corn starch | 500 g |
| Talc | 500 g |
| Calcium stearate | 25 g |

This combination of active materials is effective in reducing hypertension in adult humans. The dose is one-half to two tablets 3 times a day depending on the severity of the condition.

EXAMPLE 46

Ten thousand tablets for oral use, each containing 60 mg of 1-(2-pyrazinyl)-4-[4-[[7-(trifluoromethyl)-4-quinolinyl]amino]benzoyl]piperazine as the essential active ingredient and 25 mg melitracen, are prepared from the following ingredients and using the procedure of Example 41

| Essential active ingredient, micronized | 600 g |
|---|---|
| Melitracen, powdered | 250 g |
| Lactose | 1000 g |
| Corn starch | 500 g |
| Talc | 500 g |
| Calcium stearate | 25 g |

This tablet is useful in treating adult humans suffering from hypertension by administering 1 tablet 3 times a day.

EXAMPLE 47

Ten thousand tablets for oral use, each containing 20 mg of 4-(2-pyrimidinyl)-1-[4-[[7-(trifluoromethyl)-4-quinolinyl]amino]benzoyl]piperazine as essential active ingredient and 320 mg acetaminophen are prepared from the following ingredients and using the procedure of Example 41

| Essential active ingredient, finely powdered | 200 g |
|---|---|
| Acetaminophen, finely powdered | 3200 g |
| Corn starch | 500 g |
| Talc | 500 g |
| Calcium stearate | 50 g |

This tablet is useful in treating hypertension in an adult patient by administering one or two tablets 3 times a day, depending on the severity of the condition.

EXAMPLE 48

Following the procedure of the preceding Examples 37 to 47, inclusive, similar dosage forms are prepared by substituting an equivalent amount of the other inventive compounds or their acid addition salts, such as:

1-[benzenesulfonyl]-4-[4-[[7-(trifluoromethyl)-4-quinolinyl]amino]benzoyl]piperazine 1-[benzenesulfonyl]-4-[4-[[7-chloro-4-quinolinyl]amino]benzoyl]piperazine 1-[2-(fluorophenyl)sulfonyl]-4-[4-[[7-trifluoromethyl-4-quinolinyl]amino]benzoyl]piperazine 1-[2-(4-dimethylamino)pyrimidinyl]-4-[4-[[7-(trifluoromethyl)-4-quinolinyl]amino]benzoyl]piperazine 1-[2-triazinyl]-4-[4-[[7-chloro-4-quinolinyl]amino]benzoyl]piperazine 1-[2-(4-thiomethyl)pyridinyl]-4-[4-[[7-chloro-4-quinolinyl]amino]benzoyl]piperazine 1-[2-(4-methylpyridinyl)]-4-[4-[[7-(trifluoromethyl)-quinolinyl]amino]benzoyl]piperazine 1-[4-(2-ethyl-6-methyl)pyrimidinyl]-4-[4-[[7-(trifluoromethyl)-4-quinolinyl]amino]benzoyl]piperazine 1-[4-(2,6-dimethoxy)pyrimidinyl]-4-[4-[[7-(trifluoromethyl)-4-quinolinyl]amino]benzoyl]piperazine 1-[4-(2-methylthio)pyrimidinyl]-4-[4-[[7-(trifluoromethyl)-4-quinolinyl]amino]benzoyl]piperazine 1-(3-methoxypyrazin-2-yl)-4-[4-[[7-(trifluoromethyl)-4-quinolinyl]amino]benzoyl]piperazine 1-[(dimethylamino)sulfonyl]-4-[4-[[7-(trifluoromethyl)-4-quinolinyl]amino]benzoyl]piperazine 1-[(3-bromophenyl)sulfonyl]-4-[4-[[7-(trifluoromethyl)-4-quinolinyl]amino]benzoyl]piperazine Although not necessary in the embodiments of the inventive concept, additional active ingredients are incorporated in the present pharmaceutical dosage unit forms as desired. Each pharmaceutical dosage unit form contains therein an amount within the following non-toxic effective ranges: antihypertensive and diuretic agents such as reserpine (0.05 to 1 mg), hydralazine (10 to 100 mg), methyldopa (100 to 250 mg), guanethidine (10 to 50 mg), hydrochlorothiazide (15 to 50 mg), and ethoxzolamide (50 to 150 mg); tranquilizers, antipsychotic and anti-anxiety agents such as chlorpromazine (5 to 50 mg), thioridazine (5 to 100 mg), haloperidol (0.5 to 5 mg), meprobamate (100 to 400 mg), chlordiazepoxide (5 to 50 mg), diazepam (2 to 15 mg), and ectylurea (100 to 300 mg); barbiturates such as phenobarbital (8 to 60 mg), butabarbital (8 to 60 mg), and amobarbital (16 to 120 mg); analgesics such as aspirin (150 to 600 mg) and acetaminophen (150 to 600 mg); or antidepressants such as amitriptyline hydrochloride (10 to 50 mg), methylphenidate hydrochloride (5 to 20 mg), d-amphetamine sulfate (2 to 15 mg), methamphetamine hydrochloride (2 to 15 mg) and melitracen (15 to 50 mg).

I claim:

1. A compound of the formula II

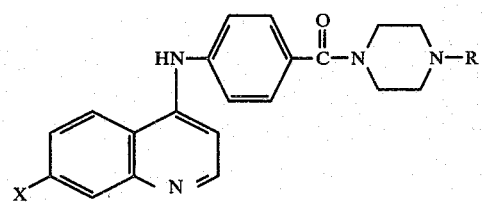

wherein X is chloro or trifluoromethyl;
wherein R is
(a) triazinyl;
(b) pyrazinyl;
(c) pyrimidinyl;
(d) triazinyl, pyrazinyl, or pyrimidinyl substituted by one or two trifluoromethyl, alkyl, alkoxy, dialkylamino, alkylthio, or halo, wherein halo is fluoro, bromo, or iodo, wherein alkyl is of one to 3 carbon atoms, and wherein alkoxy is of one to 3 carbon atoms;
(e) halopyridinyl of 1 to 4 halo atoms;
(f)

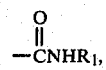

wherein $R_1$ is phenyl, phenyl subsituted with one or two halo or trifluoromethylphenyl, phenyl substituted with one or two alkoxy, alkylphenyl, or alkylphenylsulfonyl, wherein alkyl, alkoxy and halo are as defined above; or (g) —$SO_2R_2$, wherein $R_2$ is dialkylamino, phenyl substituted with one or two halo, alkylphenyl, phenyl, or trifluoromethylphenyl, or phenyl substituted with one or two alkoxy groups; wherein alkyl, alkoxy, and halo are as defined above;

or the pharmacologically acceptable acid addition salts thereof.

2. A compound according to claim 1 of the formula IIA

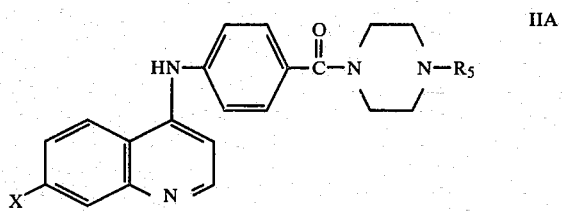

wherein X is chloro or trifluoromethyl;
wherein $R_5$ is
(a) pyrimidinyl or pyrazinyl or the alkylthio-, alkyl-, halo- or alkoxy-substituted derivatives thereof, wherein halo is chloro or fluoro and alkyl and alkoxy are of 1 to 3 carbon atoms,
(b) halopyridinyl;
(c) —$SO_2R_6$, wherein $R_6$ is phenyl, alkylphenyl, halophenyl, alkoxyphenyl, in which alkoxy, alkyl and halo are defined as above; or
(d)

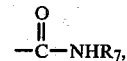

wherein $R_7$ is phenyl, alkylphenyl, halophenyl, trifluoromethylphenyl, or alkylphenylsulfonyl, wherein halo and alkyl are defined as above;
or the pharmacologically acceptable acid addition salts thereof.

3. A compound according to claim 1 of the formula IIB

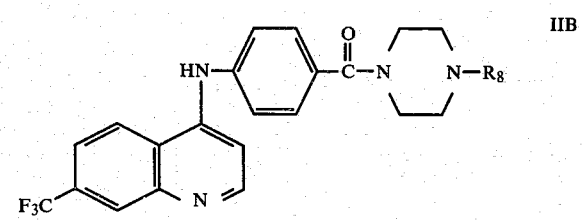

wherein $R_8$ is
(a) pyrimidinyl and pyrazinyl or these groups substituted with methyl, methylthio, methoxy or chloro;
(b) halopyridinyl;
(c) —$SO_2R_9$, wherein $R_9$ is

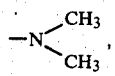

p-tolyl, p-chlorophenyl or p-fluorophenyl; or (d)

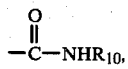

wherein $R_{10}$ is halophenyl, phenyl or trifluoromethylphenyl, wherein halo is chloro or fluoro;

or the pharmacologically acceptable acid addition salts thereof.

4. The compound according to claim 2, wherein $R_5$ is

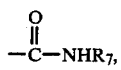

wherein $R_7$ is m-chlorophenyl and X is trifluoromethyl; 1-[[(3-chlorophenyl)amino]carbonyl]-4-[4-[[(7-trifluoromethyl)-4-quinolinyl]amino]benzoyl]piperazine.

5. A compound according to claim 3, wherein $R_8$ is

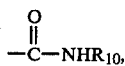

and $R_{10}$ is (m-trifluoromethyl)phenyl; 1-[[[3-(trifluoromethyl)phenyl]amino]carbonyl]-4-[4-[[(7-trifluoromethyl)-4-quinolinyl]amino]benzoyl]piperazine.

6. A compound according to claim 3, wherein $R_8$ is 2,6-dimethoxy-4-pyrimidinyl; 1-(2,6-dimethoxy-4-pyrimidinyl)-4-[4-[[7-(trifluoromethyl)-4-quinolinyl]amino]benzoyl]piperazine.

7. A compound according to claim 2, wherein X is trifluoromethyl and $R_5$ is

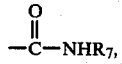

wherein $R_7$ is p-tolyl; 1-[[(4-methylphenyl)amino]carbonyl]-4-[4-[[7-(trifluoromethyl)-4-quinolinyl]amino]benzoyl]piperazine.

8. A compound according to claim 3, wherein $R_8$ is 2,3,5,6-tetrachloropyridinyl; 1-(2,3,5,6-tetrachloro-4-pyridinyl)-4-[4-[[7-(trifluoromethyl)-4-quinolinyl]amino]benzoyl]piperazine.

9. A compound according to claim 2, wherein X is trifluoromethyl and $R_5$ is $-SO_2R_6$, wherein $R_6$ is p-chlorophenyl; 1-[(4-chlorophenyl)sulfonyl]-4-[4-[[7-(trifluoromethyl)-4-quinolinyl]amino]benzoyl]piperazine.

10. A compound according to claim 2, wherein X is trifluoromethyl and $R_5$ is $-SO_2R_6$, wherein $R_6$ is p-tolylsulfonyl; 1-[[[(4-methylphenyl)sulfonyl]amino]carbonyl]-4-[4-[[7-(trifluoromethyl)-4-quinolinyl]amino]benzoyl]piperazine.

11. A compound according to claim 2, wherein X is trifluoromethyl and $R_5$ is $-SO_2R_6$, wherein $R_6$ is p-fluorophenyl; 1-[(4-fluorophenyl)sulfonyl]-4-[4-[[7-(trifluoromethyl)-4-quinolinyl]amino]benzoyl]piperazine.

12. A compound according to claim 2, wherein X is trifluoromethyl and $R_5$ is $-SO_2R_6$, wherein $R_6$ is dimethylamino; 1-[(dimethylamino)sulfonyl]-4-[4-[[7-(trifluoromethyl)-4-quinolinyl]amino]benzoyl]piperazine.

13. A compound according to clam 2, wherein X is trifluoromethyl and $R_5$ is $-SO_2R_6$, wherein $R_6$ is p-methoxyphenyl; 1-[(4-methoxyphenyl)sulfonyl]-4-[4-[[7-(trifluoromethyl)-4-quinolinyl]amino]benzoyl]piperazine.

14. A compound according to claim 3, wherein $R_8$ is 2-pyrazine; 1-(2-pyrazinyl)-4-[4-[[7-(trifluoromethyl)-4-quinolinyl]amino]benzoyl]piperazine.

15. A compound according to claim 3, wherein $R_8$ is 2-pyrimidinyl; 1-[(2-pyrimidinyl)]-4-[4-[[7-trifluoromethyl)-4-quinolinyl]amino]benzoyl]piperazine.

16. A compound according to claim 2, wherein X is trifluoromethyl and $R_5$ is $-SO_2R_6$; wherein $R_6$ is 4-methylphenyl; 1-[(4-methylphenyl)sulfonyl]-4-[4-[[7-(trifluoromethyl)-4-quinolinyl]amino]benzoyl]piperazine.

17. A compound according to claim 2, wherein X is trifluoromethyl and $R_8$ is 2-methylthio-4-pyrimidinyl; 1-[4-(2-methylthio)-pyrimidinyl]-4-[4-[[7-(trifluoromethyl)-4-quinolinyl]amino]benzoyl]piperazine.

18. A pharmaceutical dosage unit form for systemic administration to alleviate hypertension consisting essentially of an effective non-toxic amount of a compound of the formula

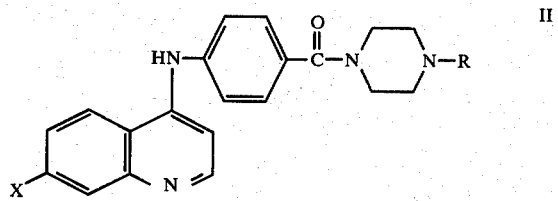

wherein X is chloro or trifluoromethyl;

wherein R is (a) triazinyl;

(b) pyrazinyl;

(c) pyrimidinyl;

(d) triazinyl, pyrazinyl, or pyrimidinyl substituted by one or two trifluoromethyl, alkyl, alkoxy, dialkylamino, alkylthio, or halo, wherein halo is fluoro, bromo, or iodo, wherein alkyl is of one to 3 carbon atoms, and wherein alkoxy is of one to 3 carbon atoms;

(e) halopyridinyl of 1 to 4 halo atoms;

(f)

wherein $R_1$ is phenyl, phenyl substituted with one or two halo or trifluoromethylphenyl, phenyl substituted with one or two alkoxy, alkylphenyl, or alkylphenylsulfonyl, wherein alkyl, alkoxy and halo are as defined above; or (g) $-SO_2R_2$, wherein $R_2$ is dialkylamino, phenyl substituted with one or two halo, alkylphenyl, phenyl, or trifluoromethylphenyl, or phenyl substituted with one or two alkoxy groups; wherein alkyl, alkoxy, and halo are as defined above;

or the pharmacologically acceptable acid addition salts thereof.

19. The composition according to claim 18, wherein the compound used in effective non-toxic amount is that of the formula IIA

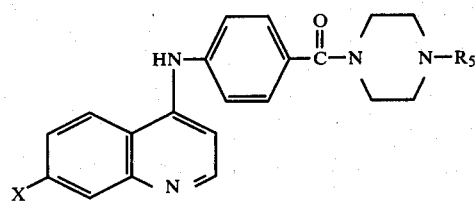

wherein X is chloro or trifluoromethyl;
wherein $R_5$ is
(a) pyrimidinyl or pyrazinyl or the alkylthio-, alkyl-, halo- or alkoxy-substituted derivatives thereof, wherein halo is chloro or fluoro and alkyl and alkoxy are of 1 to 3 carbon atoms,
(b) halopyridinyl;
(c) —$SO_2R_6$, wherein $R_6$ is phenyl, alkylphenyl, halophenyl, alkoxyphenyl, in which alkoxy, alkyl and halo are defined as above; or
(d)

wherein $R_7$ is phenyl, alkylphenyl, halophenyl, trifluoromethylphenyl, or alkylphenylsulfonyl, wherein halo and alkyl are defined as above; or the pharmacologically acceptable acid addition salts thereof.

20. The composition according to claim 18, wherein the compound used in effective non-toxic amount is that of formula IIB

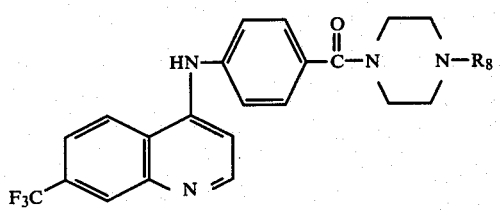

wherein $R_8$ is
(a) pyrimidinyl and pyrazinyl or these groups substituted with methyl, methylthio, methoxy or chloro;
(b) halopyridinyl;
(c) —$SO_2R_9$, wherein $R_9$ is

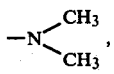

p-tolyl, p-chlorophenyl or p-fluorophenyl; or
(d)

wherein $R_{10}$ is halophenyl, phenyl or trifluoromethylphenyl, wherein halo is chloro or fluoro;
or the pharmacologically acceptable acid addition salts thereof.

21. The composition according to claim 19, wherein the compound used in effective non-toxic amount is 1-(2,6-dimethoxy-4-pyrimidinyl)-4-[4-[[7-(trifluoromethyl)-4-quinolinyl]amino]benzoyl]piperazine.

22. The composition according to claim 19, wherein the compound used in effective non-toxic amount is 1-(2-pyrimidinyl)-4-[4-[[7-(trifluoromethyl)-4-quinolinyl]amino]benzoyl]piperazine.

23. The composition according to claim 19, wherein the compound used in effective non-toxic amount is 1-(2-pyrazinyl)-4-[4-[[7-(trifluoromethyl)-4-quinolinyl]amino]benzoyl]piperazine.

24. The composition according to claim 20, wherein the compound used in effective non-toxic amount is 1-[(4-methylphenyl)sulfonyl]-4-[4-[[7-(trifluoromethyl)-4-quinolinyl]amino]benzoyl]piperazine.

25. The composition according to claim 20, wherein the compound used in effective non-toxic amount is 1-[(4-chlorophenyl)sulfonyl]-4-[4-[[7-(trifluoromethyl)-4-quinolinyl]amino]benzoyl]piperazine.

26. The composition according to claim 20, wherein the compound used in effective non-toxic amount is 1-[(4-fluorophenyl)sulfonyl]-4-[4-[[7-(trifluoromethyl)-4-quinolinyl]amino]benzoyl]piperazine.

27. The composition according to claim 20, wherein the compound used in effective non-toxic amount is 1-[[(3-chlorophenyl(amino]carbonyl]-4-[4-[[(7-trifluoromethyl)-4-quinolinyl]amino]benzoyl]piperazine.

28. The composition according to claim 20, wherein the compound used in effective non-toxic amount is 1-[[[3-(trifluoromethyl)phenyl]amino]carbonyl]-4-[4-[[7-(trifluoromethyl)-4-quinolinyl]amino]benzoyl]piperazine.

29. A method of obtaining antihypertensive effects in a mammal which consists essentially of administering systemically to the mammal a pharmaceutical dosage unit form supplying an effective non-toxic amount for hypertensive effects of a compound of the formula II

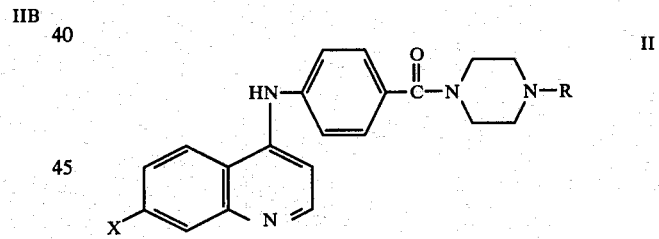

wherein X is chloro or trifluoromethyl;
wherein R is
(a) triazinyl;
(b) pyrazinyl;
(c) pyrimidinyl;
(d) triazinyl, pyrazinyl, or pyrimidinyl substituted by one or two trifluoromethyl, alkyl, alkoxy, dialkylamino, alkylthio, or halo, wherein halo is fluoro, bromo, or iodo, wherein alkyl is of one to 3 carbon atoms, and wherein alkoxy is of one to 3 carbon atoms;
(e) halopyridinyl of 1 to 4 halo atoms;
(f)

wherein $R_1$ is phenyl, phenyl substituted with one or two halo or trifluoromethylphenyl, phenyl substituted with one or two alkoxy, alkylphenyl, or alkylphenylsulfonyl, wherein alkyl, alkoxy and halo are as defined above; or (g) —SO$_2$R$_2$, wherein R$_2$ is dialkylamino, phenyl substituted with one or two halo, alkylphenyl, phenyl, or trifluoromethylphenyl, or phenyl substituted with one or two alkoxy groups; wherein alkyl, alkoxy, and halo are as defined above;

or the pharmacologically acceptable acid addition salts thereof.

30. A method according to claim 29, wherein the compound is of the formula IIA

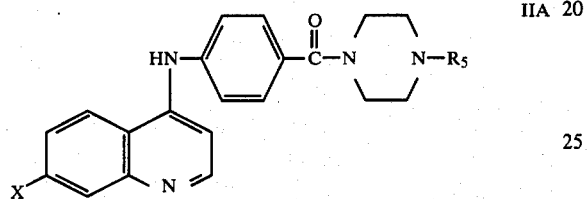

wherein X is chloro or trifluoromethyl;
wherein R$_5$ is (a) pyrimidinyl or pyrazinyl or the alkylthio-, alkyl-, halo- or alkoxy-substituted derivatives thereof, wherein halo is chloro or fluoro and alkyl and alkoxy are of 1 to 3 carbon atoms, (b) halopyridinyl;

(c) —SO$_2$R$_6$, wherein R$_6$ is phenyl, alkylphenyl, halophenyl, alkoxyphenyl, in which alkoxy, alkyl and halo are defined as above; or (d)

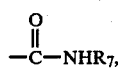

wherein R$_7$ is phenyl, alkylphenyl, halophenyl, trifluoromethylphenyl, or alkylphenylsulfonyl, wherein halo and alkyl are defined as above;

or the pharmacologically acceptable acid addition salts thereof.

31. A method according to claim 29, wherein the compound is of the formula IIB

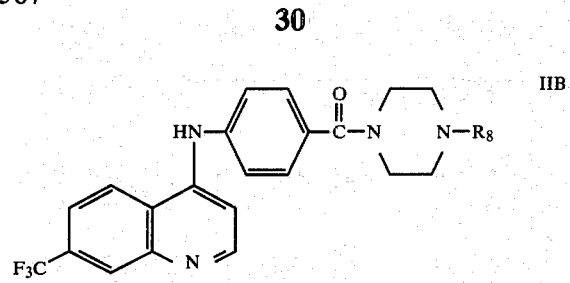

wherein R$_8$ is (a) pyrimidinyl and pyrazinyl or these groups substituted with methyl, methylthio, methoxy or chloro;

(b) halopyridinyl;

(c) —SO$_2$R$_9$, wherein R$_9$ is

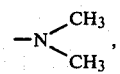

p-tolyl, p-chlorophenyl or p-fluorophenyl; or (d)

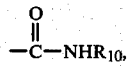

wherein R$_{10}$ is halophenyl, phenyl or trifluoromethylphenyl, wherein halo is chloro or fluoro; or the pharmacologically acceptable acid addition salts thereof.

32. A method according to claim 30, wherein the compound is 1-(2,6-dimethoxy-4-pyrimidinyl)-4-[4-[[7-(trifluoromethyl)-4-quinolinyl]amino]benzoyl]piperazine.

33. A method according to claim 30, wherein the compound is 1-(2-pyrazinyl)-4-[4-[[7-(trifluoromethyl)-4-quinolinyl]amino]benzoyl]-piperazine.

34. A method according to claim 30, wherein the compound is 1-[(2-pyrimidinyl)]-4-[4-[[7-(trifluoromethyl)-4-quinolinyl]amino]benzoyl]piperazine.

35. A method according to claim 31, wherein the compound is 1-[(4-methylphenyl)sulfonyl]-4-[4-[[7-(trifluoromethyl)-4-quinolinyl]amino]benzoyl]piperazine.

36. A method according to claim 31, wherein the compound is 1-[(4-chlorophenyl)sulfonyl]-4-[4-[[7-(trifluoromethyl)-4-quinolinyl]amino]benzoyl]piperazine.

37. A method according to claim 31, wherein the compound is 1-[(4-fluorophenyl)sulfonyl]-4-[4-[[7-(trifluorometyl)-4-quinolinyl]amino]benzoyl]piperazine.

38. A method according to claim 31, wherein the compound is 1-[[(3-chlorophenyl)amino]carbonyl]-4-[4-[[7-trifluoromethyl)-4-quinolinyl]amino]benzoyl]piperazine.

39. A method according to claim 31, wherein the compound is 1-[[(3-trifluoromethylphenyl)amino]carbonyl]-4-[4-[[7-(trifluoromethyl)-4-quinolinyl]amino]benzoyl]piperazine.

* * * * *

UNITED STATES PATENT OFFICE
CERTIFICATE OF CORRECTION

Patent No. 4,167,567            Dated  11 September 1979

Inventor(s)  John M. McCall

It is certified that error appears in the above-identified patent and that said Letters Patent are hereby corrected as shown below:

In the Abstract (second column, line 16), "$R_1$ is dialkylamino," should read -- $R_2$ is dialkylamino, --;

Column 2, line 51, "cimbintions" should read -- combinations --;

Column 3, line 18, "$R^5$ is $-SO_2R_6$," should read -- $R_5$ is $-SO_2R_6$, --;

Column 6, lines 7-8, "with g ze-wrapped paper" should read -- with gauze-wrapped paper --;  line 25, in column for "Slightly Pink" "5.5" should read -- 6.5 -- and in column for "Orange" -- 5.5 -- should appear Column 5, line 68, "greed of" should read -- freed of --;

Column 15, line 41, "$C_{29}C_{26}F_3N_5O_2$" should read -- $C_{29}H_{26}F_3N_5O_2$ --;

Column 17, line 12, "1-[2-(4-methylpyridinyl)-4-[[7-chloro-4-quinolinyl-" should read -- 1-[2-(4-methylpyridinyl-4-[4-[[7-chloro-4-quinolinyl- --;

Column 18, line 68, "1-[[unsubstituted amino]" should read -- 1-[[substituted amino] --;

Column 20, line 43, "Deionized water, g.s." should read -- Deionized water q.s. --;

Column 23, line 64, Column 26, line 47, and Column 28, line 57, "fluoro, bromo, or iodo," should read -- fluoro, bromo, or chloro, --;

Column 24, line 7, Column 26, line 58, and Column 28, line 68, "or two halo or trifluoromethylphenyl," should read -- or two halo, trifluoromethylphenyl, --.

*Signed and Sealed this*

*Twentieth* Day of *October 1981*

[SEAL]

*Attest:*

GERALD J. MOSSINGHOFF

*Attesting Officer*    *Commissioner of Patents and Trademarks*